US011633352B2

United States Patent
Ehrenpreis

(10) Patent No.: US 11,633,352 B2
(45) Date of Patent: *Apr. 25, 2023

(54) DICLOFENAC AND HYALURONIC ACID COMBINATION TREATMENT FOR ORAL LEUKPOPLAKIA

(71) Applicant: Eli D. Ehrenpreis, Skokie, IL (US)

(72) Inventor: Eli D. Ehrenpreis, Skokie, IL (US)

(73) Assignee: E2Bio Life Science, LLC, Skokie, IL (US)

( * ) Notice: Subject to any disclaimer, the term of this patent is extended or adjusted under 35 U.S.C. 154(b) by 500 days.

This patent is subject to a terminal disclaimer.

(21) Appl. No.: 16/776,984

(22) Filed: Jan. 30, 2020

(65) Prior Publication Data

US 2020/0179268 A1    Jun. 11, 2020

Related U.S. Application Data

(63) Continuation-in-part of application No. 16/242,131, filed on Jan. 8, 2019, now Pat. No. 11,229,578.

(60) Provisional application No. 62/800,151, filed on Feb. 1, 2019, provisional application No. 62/615,107, filed on Jan. 9, 2018.

(51) Int. Cl.

| | |
|---|---|
| *A61K 31/196* | (2006.01) |
| *A61K 31/728* | (2006.01) |
| *A61K 47/32* | (2006.01) |
| *A61K 47/44* | (2017.01) |
| *A61K 9/06* | (2006.01) |
| *A61K 9/00* | (2006.01) |
| *A61J 7/00* | (2006.01) |
| *A61K 47/02* | (2006.01) |

(52) U.S. Cl.
CPC ............ *A61K 9/006* (2013.01); *A61J 7/0053* (2013.01); *A61K 9/06* (2013.01); *A61K 31/196* (2013.01); *A61K 31/728* (2013.01); *A61K 47/02* (2013.01); *A61K 47/32* (2013.01); *A61K 47/44* (2013.01)

(58) Field of Classification Search
CPC ...... A61K 31/196; A61K 31/728; A61K 9/06; A61K 47/32; A61K 47/44
See application file for complete search history.

(56) References Cited

U.S. PATENT DOCUMENTS

| 4,051,234 A | 9/1977 | Gieske | |
|---|---|---|---|
| 2004/0005277 A1 | 1/2004 | Willison | |
| 2005/0136381 A1 | 6/2005 | Andersen | |
| 2008/0044797 A1* | 2/2008 | Bardach | A61C 19/063 433/217.1 |
| 2009/0017422 A1* | 1/2009 | Creamer | A61C 19/066 433/215 |

FOREIGN PATENT DOCUMENTS

| WO | 19970003699 | 6/1997 |
|---|---|---|
| WO | 2013037457 | 3/2013 |

OTHER PUBLICATIONS

International Preliminary Report on Patentability, dated May 27, 2020; PCT/US2020/016003—related application.
Lima, G.S. et al., "Diclofenac in hyaluronic acid gel: an alternative treatment for actinic cheilitis", J Appl. Oral Sci., 2010, vol. 18, No. 6, pp. 633-637 abstract: pp. 633-636.

\* cited by examiner

*Primary Examiner* — Samira J Jean-Louis
(74) *Attorney, Agent, or Firm* — Adam K. Sacharoff; Much Shelist, P.C.

(57) ABSTRACT

An oral gel composition suitable for the treatment of oral leukoplakia comprising a combination of diclofenac with hyaluronic acid and methods of administering the oral gel that may include a device that prolongs contact time of the oral gel with the areas of the mucosa that are affected by oral leukoplakia.

9 Claims, 12 Drawing Sheets

DICLOFENAC AND HYALURONIC ACID COMBINATION TREATMENT FOR ORAL LEUKPOPLAKIA

CROSS REFERENCE TO RELATED INVENTIONS

The present application claims priority to U.S. Provisional Application 62/800,151 filed Feb. 1, 2019; and is a Continuation in Part of U.S. application Ser. No. 16/242,131 filed Jan. 8, 2019, which claims priority to U.S. Provisional Application 62/615,107 filed Jan. 9, 2018.

BACKGROUND OF THE INVENTION

Oral leukoplakia is defined as an abnormal whitish area that presents in the oral mucosa. It is a precursor lesion for the development of oral cancer. Oral leukoplakia can occur in patients at high risk for oral cancer, including those smoking and chewing tobacco, heavy alcohol consumers and chewers of betel nuts. These substances produce irritation and chronic inflammation in areas of oral mucosa which may lead to oral leukoplakia. Even ill-fitting dentures or misaligned teeth that are pressing against adjacent oral mucosa may induce oral leukoplakia via an irritative mechanism. Approximately 1-2% of the world population has oral leukoplakia. The most common locations of oral leukoplakia in the mouth are the buccal mucosa (76%), alveolar sulcus (19%), and the tongue (5%).

Almost all oral cancers begin as precancerous lesions. Since the diagnosis of oral leukoplakia represents an opportunity to identify patients at risk for oral cancer, and treatment of oral leukoplakia has the potential to prevent oral cancer in these patients, a number of interventions for lessening the severity or elimination of oral leukoplakia have been studied. These include surgical removal of lesions, laser therapy, and systemic treatment with retinoids, carotenoids, celecoxib, and a Bowman-Birk inhibitor. Topical bleomycin has also been tried. According to a recent Cochrane Review, only orally administered vitamin A and beta carotene possibly have some effect in healing oral lesions, but there is a lack of evidence of any treatment that is effective for preventing the development of oral cancer in patients with oral leukoplakia. Thus, a need remains for effective treatments for oral leukoplakia and prevention of oral cancer.

SUMMARY OF THE INVENTION

A first aspect of the present invention is directed to an aqueous oral gel composition for the treatment of oral leukoplakia, comprising a therapeutically effective amount of a nonsteroidal anti-inflammatory drug (NSAID) or a pharmaceutically acceptable salt thereof, a therapeutically effective amount of hyaluronic acid or a pharmaceutically acceptable salt thereof, a gelling agent or thickener, a flavoring agent and/or sweetener. In some embodiments, the composition may include at least one additional orally acceptable excipient such as a preservative, a colorant, a neutralizing base, and a solubilizing or wetting agent.

In some embodiments, the NSAID is diclofenac or a pharmaceutically acceptable salt thereof.

In some embodiments, the oral gel composition comprises a combination of diclofenac or a pharmaceutically acceptable salt thereof in an amount of about 0.1% to about 15% w/w and hyaluronic acid or a pharmaceutically acceptable salt thereof in the amount of about 0.1% to about 10% w/w.

In some embodiments, the oral gel composition comprises a combination of diclofenac or a pharmaceutically acceptable salt thereof in an amount of about 0.5% to about 6% w/w and hyaluronic acid or a pharmaceutically acceptable salt thereof in the amount of about 1.0% to about 5% w/w.

Another aspect of the present invention is directed to a method of delivering the anti-leukoplakia oral gel composition described herein to the mucosal tissue of a patient or subject having oral leukoplakia or who is a risk of developing oral leukoplakia, which comprises: administering a therapeutically effective amount of the oral gel composition to the mucosal tissue or the affected portion thereof.

In some embodiments, the patient who is at risk of developing oral leukoplakia may be a heavy user of tobacco or alcohol, or may be undergoing an event that subjects to the patient or subject to risk of developing oral leukoplakia, such as poor dental hygiene, in which case the therapeutically effective amount of the anti-leukoplakia oral gel composition may inhibit or delay the onset of oral leukoplakia.

In some embodiments, the method may include use of an oral device comprising: an oral retention portion that is suitably shaped to be retained in the oral cavity for a predetermined treatment period and a covering portion that has at least one surface that contacts the mucosal tissue or the affected portion thereof being treated with the oral gel composition, which in some embodiments may include the tongue (e.g., ventral surface and one or both sides thereof).

In some embodiments, the method is practiced with an oral device that comprises: a fitting portion having an arcuate shape corresponding to the dental arche of the patient and at least one covering portion, the covering portion having a respective outer surface, an upper wing portion and a lower wing portion; at least one bite flange extending from an interior surface of the fitting portion; an upper ledge extending from the interior surface of the fitting portion and following the arc of the fitting portion, wherein an upper surface of the upper ledge and an upper surface of the at least one bite flange are continuous with one another, wherein the at least one covering section is more flexible than the fitting portion, and wherein a portion of the respective outer surface of the at least one covering portion is in contact with the portion of the mucosal tissue. The at least one covering portion has a surface that contacts and rests against the tongue (e.g., dorsal, ventral or sides). The device constitutes yet another aspect of the present invention.

Thus, in some embodiments, the method comprises applying the oral gel composition to the portion of the mucosal tissue prior to inserting the device in the mouth of the patient. In some embodiments, the method comprises applying the oral gel composition to the outer surface of the device prior to inserting the device in the mouth of the patient. In some embodiments, the method comprises: applying a first amount of the oral gel composition to the portion of the mucosal tissue; and applying a second amount of the oral gel composition to the outer surface of the device and inserting the device in the mouth of the patient.

Another aspect of the present invention is directed to a kit. The kit may include an oral gel composition described herein dispensed in a suitable package such as a squeezable tube; a device, comprising a fitting portion having an arcuate shape corresponding to the dental arche of the patient; at least one covering portion defined on the fitting portion, the covering portion having a respective outer surface, an upper wing portion and a lower wing portion; at least one bite flange extending from an interior surface of the fitting portion; and an upper ledge extending from the interior surface of the fitting portion and following the arc of the fitting portion, wherein an upper surface of the upper ledge and an upper surface of the at least one bite flange are continuous with one another, and wherein the at least one covering section is more flexible than the fitting portion, and wherein the at least one covering portion may also have a surface that contacts and rests against the tongue (e.g., dorsal, ventral or sides) and floor of the mouth between the lower teeth and the tongue; and printed instructions on how to use the device to administer the oral gel composition to the mucosal tissue of the patient. In some embodiments, the kit may also include an applicator (e.g., oral swab, Toothette®, and blu®m oral gel applicator) for applying the medication onto the mucosa that is affected by oral leukoplakia.

BRIEF DESCRIPTION OF THE FIGURES

Various aspects of the disclosure are discussed herein with reference to the accompanying Figures. It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. For purposes of clarity, however, not every component may be labeled in every drawing. The Figures are provided for the purposes of illustration and explanation and are not intended as a definition of the limits of the disclosure. In the Figures.

DETAILED DESCRIPTION

Figure 1:
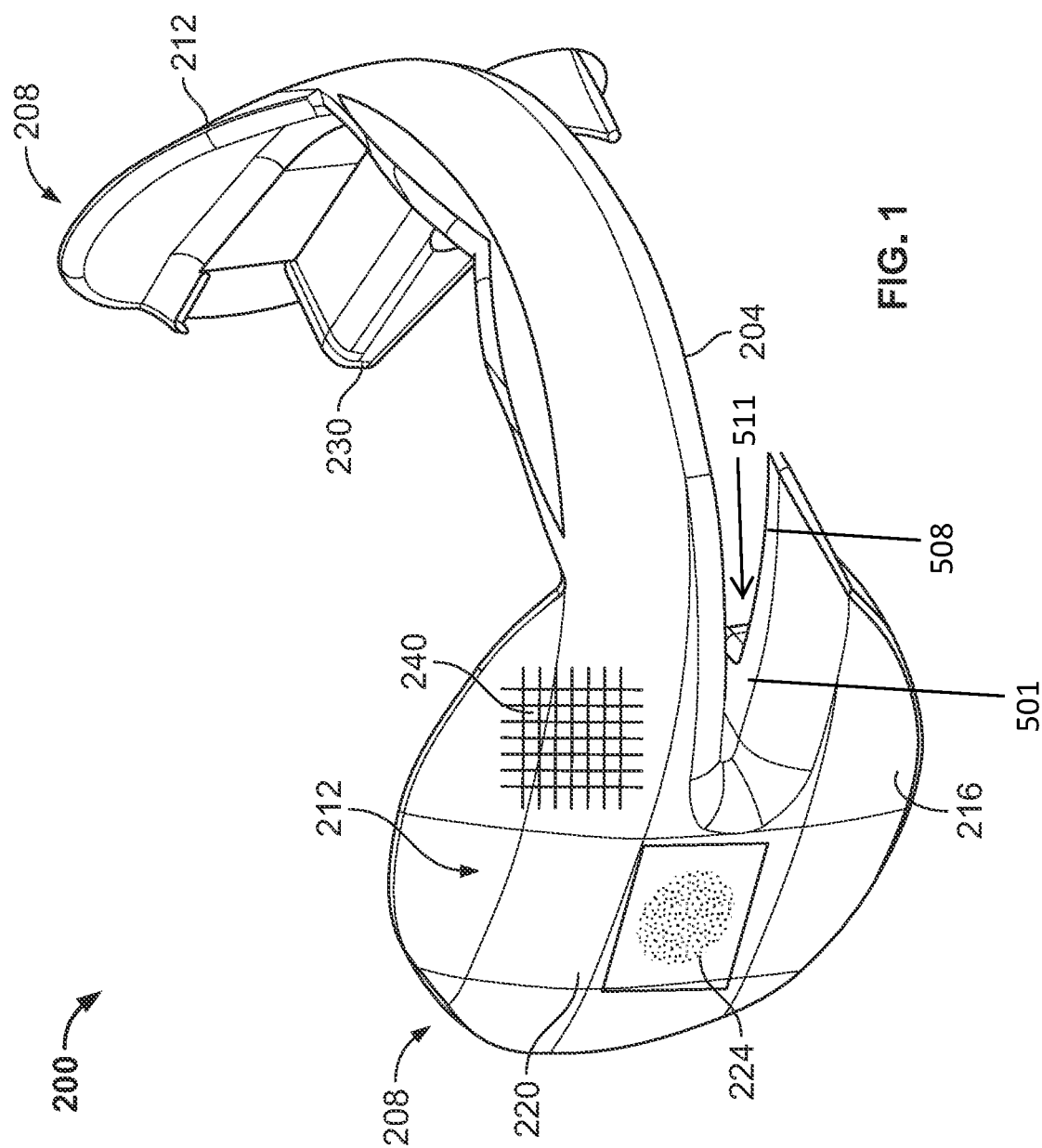
FIG. 1 is a front perspective view of a leukoplakia treatment device, in accordance with an aspect of the present disclosure.

In the following detailed description, particulars are set forth in order to provide a thorough understanding of the aspects of the disclosure. It will be understood by those of ordinary skill in the art that these may be practiced without some of these specific details. In other instances, well-known methods, procedures, components and structures may not have been described in detail so as not to obscure the aspects of the disclosure.

It is to be understood that the present disclosure is not limited in its application to the details of construction and the arrangement of the components or steps set forth in the following description or illustrated in the drawings as it is capable of implementations or of being practiced or carried out in various ways. Also, it is to be understood that the phraseology and terminology employed herein are for description only and should not be regarded as limiting.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject" and "patient" are used interchangeably herein and describe a person prone to or at risk of developing oral leukoplakia, or who is suffering from oral leukoplakia. A subject "in need of the treatment" may have been positively diagnosed or otherwise presents with a sufficient number of risk factors, or a sufficient number or combination of signs or symptoms such that a medical professional could diagnose or suspect that the subject was suffering from oral leukoplakia. Thus, subjects suffering from, and suspected of suffering from, oral leukoplakia are not necessarily two distinct groups. Patients or subjects who are prone to or at risk of developing oral leukoplakia may have a prior history of cancer of the head and neck or esophagus or may be tobacco chewers or smokers, chewers of betel nuts, users of large amounts of alcohol, or those with a history of oral human papilloma virus (HPV) infection.

Broadly, the present invention is directed to an aqueous oral gel composition for the treatment of oral leukoplakia comprising a nonsteroidal anti-inflammatory drug (NSAID) or a pharmaceutically acceptable salt thereof, hyaluronic acid or a pharmaceutically acceptable salt thereof, a gelling agent or thickener, a flavoring agent and/or sweetener. In some embodiments, the composition may include at least one additional orally acceptable excipient such as a preservative, a, a neutralizing base, and a solubilizing or wetting agent.

In some embodiments, the NSAID is selected from the group consisting of: aspirin, celecoxib, diclofenac, diflunisal, etodolac, ibuprofen, indomethacin, ketoprofen, ketorolac, nabumetone, naproxen, oxaprozin, piroxicam, salsalate, sulindac, and tolmetin.

In some embodiments, the NSAID is diclofenac or a pharmaceutically acceptable salt thereof.

The amount of diclofenac or a pharmaceutically acceptable salt thereof may vary depending upon factors such as the severity of oral leukoplakia (e.g., its present status); the age, body weight, general health, sex and diet of the subject; drugs used in combination or coincidental with the specific compound employed; and like factors well known in the medical arts (see, for example, Goodman and Gilman's, "The Pharmacological Basis of Therapeutics", 10th Edition, A Gilman, J. Hardman and L. Limbird, eds., McGraw-Hill Press, 155-173, 2001). In general, the amount of diclofenac or a pharmaceutically acceptable salt thereof is about 0.1% to about 15% w/w, and in some embodiments from about 0.5% to about 6% w/w, based on the total weight of the oral gel composition.

The amount of hyaluronic acid or a pharmaceutically acceptable salt thereof may vary depending upon factors such as the severity of oral leukoplakia (e.g., its present status); the age, body weight, general health, sex and diet of the subject; drugs used in combination or coincidental with the specific compound employed; and like factors well known in the medical arts. In general, the amount of hyaluronic acid or a pharmaceutically acceptable salt thereof is about 0.1% to about 10% w/w, and in some embodiments from about 1.0% to about 5 w/w, based on the total weight of the oral gel composition.

The NSAID (e.g., diclofenac) and hyaluronic acid may be in the form of pharmaceutically acceptable salts. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

The gelling agents may be natural or synthetic. Hydrophilic gelling agents may be particularly suitable for use in the invention. Representative examples of gelling agents or thickeners that may be suitable for use in the present invention include synthetic hectorite, which is a synthetic colloidal magnesium alkali metal silicate complex clay (commercially available as Laponite® (e.g., CP, SP 2002, or D)), carboxyvinyl polymers (e.g., polycarbophil) commercially available as which may also provide antibacterial properties, poloxamers (e.g., Polox®), Irish moss, i-carrageenan, gum tragacanth, starch, polyvinyl alcohol (PVA), polyvinylpyrrolidone, Pentravan®, hydroxyethylpropyl-cellulose, hydroxybutyl methyl cellulose, hydroxypropyl methyl cellulose, hydroxyethyl cellulose (e.g., Natrosol™), and sodium carboxymethyl cellulose or cellulose gum and colloidal silica such as those available as finely ground Syloid® (244) and Sylox®.

Amounts of the gelling agent or thickener may vary depending upon several factors that may include the desired viscosity (e.g., about 150×10³ to about 360×10³ cP, and in some embodiments from about 200×10³ to about 300×10³ cP). In some embodiments, the amount of gelling agent or thickener is from about 0.2% to about 10% w/w, and in some embodiments from about 2% to about 5% w/w.

The gel compositions include water in amounts that generally vary from about 20% to about 80% w/w.

Representative examples of flavoring or sweetening agents that may be suitable for use in the present invention include oil of wintergreen, oil of peppermint, oil of spearmint, oil of sassafras, clove bud oil, cassia, sage, parsley oil, marjoram, lemon, orange, cis-jasmone, 2,5-dimethyl-4-hydroxy-3(2H)-furanone, 5-ethyl-3-hydroxy-4-methyl-2(5H)-furanone, vanillin, ethyl vanillin, an isaldehyde, 3,4-methylenedioxybenzaldehyde, 3,4-dimethoxybenzaldehyde, 4-hydroxybenzaldehyde, 2-methoxybenzaldehyde, benzaldehyde; cinnamaldehyde, hexyl cinnamaldehyde, alpha-methyl cinnamaldehyde, ortho-methoxy cinnamaldehyde, alpha-amyl cinnamaldehydepropenyl guaethol, heliotropine, 4-cis-heptenal, diacetyl, methyl-p-tert-butyl phenyl acetate, menthol, methyl salicylate, ethyl salicylate, 1-menthyl acetate, oxanone, alpha-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, alpha-terpineol, linalool, limonene, citral, maltol, ethyl maltol, anethole, dihydroanethole, carvone, menthone, damascenone, ionone, gamma decalactone, gamma nonalactone, and gamma undecalactone and mixtures thereof. Generally suitable flavoring ingredients are those containing structural features and functional groups that are less prone to redox reactions. Sweetening agents which can be used include saccharin, dextrose, levulose and sodium cyclamate. The amount of flavoring and sweetening agents may vary, e.g., in amounts from about 0.005% to about 2% w/w.

The oral gel compositions may further include one or more orally acceptable excipients.

The oral gel composition may also include a solubilizing or wetting agent which may assist in dissolving the active anti-leukoplakia agents, particularly in the presence of saliva. Representative examples of such effective solubilizing agents include humectant polyols such as propylene glycol, dipropylene glycol, PEG 40 or polyethylene glycol of other molecular weights, hydrogenated castor oil, glycerin, PEG 40 hydrogenated castor oil, glycerin, sorbitol, xylitol, butylene glycol, and hexylene glycol cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate. Lipoil®, a penetration enhancing mixture oflecithin and isopropyl palmitate, may also be used as solubilizing agent. The amount of solubilizing agent may vary, e.g., in amounts from about 1.0% to about 20% w/w.

The oral gel composition described herein may contain a surface-active agent or surfactant. Surface-active agents may be anionic, nonionic or ampholytic (amphoteric) in nature. Representative examples of anionic surfactants that may be suitable for use in the present invention include water-soluble salts of higher fatty acid monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, higher fatty esters oftaurine and the substantially saturated higher aliphatic acyl amides oflower aliphatic amino carboxylic acid compounds, such as those having 12 to 16 carbons in the fatty acid, alkyl or acyl radicals, and the like. Examples of the aforementioned taurines and amides are N-methyl-N-cocoyl taurate, N-methyl-N-oleoyl taurate, N-methyl-N-palmitoyl taurate, N-lauroyl sarcosine, and the sodium, potassium, and ethanolamine salts ofN-lauroyl, N-myristoyl, or N-palmitoyl sarcosine which should be substantially free from soap or similar higher fatty acid material. Representative examples of nonionic surfactants that may be suitable for use in the present invention include condensation products of ethylene oxide with various reactive hydrogen-containing compounds reactive therewith having long hydrophobic chains (e.g., aliphatic chains of about 12 to 20 carbon atoms), which condensation products ("ethoxamers") contain hydrophilic polyoxyethylene moieties, such as condensation products of poly(ethylene oxide) with fatty acids, fatty alcohols, fatty amides, polyhydric alcohols (e.g., sorbitan monosterate) and polypropyleneoxide (e.g., Pluronice materials). Representative examples of ampholytic surfactants that may be suitable for use in the present invention include derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of the suitable nonionic and amphoteric surfactants are disclosed by Gieske et al., U.S. Pat. No. 4,051,234. Surface active agents or surfactants are typically present in amount of about 0.1% to about 5% by weight, and in some embodiments from about 0.7% to about 2% by weight, based on the total weight of the composition.

The gel compositions may include a preservative. Suitable preservatives include sodium benzoate, benzoic acid, diazolinyl urea, imidazolinyl urea, benzalkonium chloride, parabens, chlorhexidine acetate, chlorhexidine gluconate, citric acid, sorbic acid, potassium sorbitol, ethanol, dichlorobenzyl alcohol, chlorbutanol and phenoxyethanol. Suitable preservatives are typically present in amount of about 0.01% to about 0.5% by weight, based on the total weight of the composition.

The gel compositions may include a colorant. Any one of commercially available FDA approved colorants may be used. Examples of colorants include titanium dioxide, Acid Blue 9, FD&C Green 3, FD&C Red 3 and FD&C Red 4. Colorants are typically present in amount of about 0.10% to about 5% by weight, and in some embodiments from about 0.5% to about 2% by weight, based on the total weight of the composition.

The gel compositions may include a neutralizing base to adjust pH to about 6 to about 8. Sodium hydroxide is an example of neutralizing base.

In some embodiments, the oral gel composition may include diclofenac USP 3.6 g (3% w/w), hyaluronic acid 240 mg (0.2% w/w), ethanol 200 proof 4.8 mL, Lipoil® 28.8 mL, Polox® 20% gel q.s. ad (as much as is sufficient) 120 g, peppermint oil 2 mL, and Acid Blue 9 to the desired color.

In some embodiments, the oral get composition may include diclofenac 3 g (3% w/w), hyaluronic 0.2% (200 mg), Pentravan® q.s. ad 90 g, water 9 g, xylitol 7.5% (9 g), polyethelyene glycol to form paste, Acid Blue 9 to desired color and 0.5 ml 0.2% peppermint oil or oil of spearmint.

In some embodiments, the oral gel composition may include diclofenac 3 g (3% w/w), glycerin 4 g, sodium saccharate 50 mg, peppermint oil 0.02 mL, 0.2% hyaluronic acid 20 mg (0.2% w/w) and hydroxyethylcellulose 2% gel 100 g.

Oral gels of the present invention may be prepared in accordance with standard techniques.

As used herein, the term, "therapeutically effective amount" refers to an amount of the oral gel composition and the active agents therein that is/are effective in producing the desired therapeutic response in a particular patient suffering from oral leukoplakia. The term "therapeutically effective amount" thus includes the amount of the oral gel composition and the active agents therein that when administered, may induce a positive modification in oral leukoplakia, or is sufficient to prevent development or progression of oral leukoplakia, or alleviate to some extent, one or more of the symptoms of oral leukoplakia, or which simply kills or inhibits the growth of diseased cells.

Another aspect of the present invention is directed to a method of delivering the oral gel composition described herein to the mucosal tissue of a patient or subject or an affected portion thereof, which comprises: administering a therapeutically effective amount of the oral gel composition to the mucosal tissue or an affected portion thereof which comprises; inserting, in the mouth of the patient, a device comprising: an oral retention portion that is suitably shaped to be retained in the oral cavity for a predetermined treatment period and a covering portion that has at least one surface that contacts the mucosal tissue being treated with the oral gel composition.

The combination of the anti-leukoplakia oral gel composition described herein, and the device may increase the retention time of the active agents on the affected mucosal tissue, which in turn may enhance the efficacy of the agent.

In some embodiments the oral gel composition may be administered topically in the mouth, followed by placement of the device that is brought into direct contact with and covers the treated mucosal tissue. In other embodiments, the oral gel may be applied to or coated onto, the device beforehand. This approach may also provide a more targeted delivery of the agent to the affected mucosal tissue, as well as an increase in retention time. In yet other embodiments, the oral gel composition may be applied to the affected tissue, followed by insertion of the device having additional oral gel composition dispersed therein.

The device is configured so as to be comfortably held in the mouth for prolonged periods of time and therefore extend the contact time of the oral gel composition or active agents therein on the oral mucosa or affected portions thereof. Thus, the present methods may provide one or more advantages such as an increase in the concentration and duration of contact of the oral gel composition described herein with the area(s) of mucosa that is/are, or could be affected with oral leukoplakia; a decrease in systemic toxicity of the active agents since the agents may be administered in lower doses that will remain within the oral cavity longer and will, therefore, have lower systemic absorption from being swallowed; and further an increase in topical pharmacologic activity at the site of release, i.e., the oral mucosa, compared to conventional methods of direct delivery of substances onto the oral mucosa such as spray and gel forms of these medications. Once the device is removed, the remaining medication may be washed away or left in place.

Our group has performed an initial Phase I trial to test the tolerability of the use of diclofenac gel and an oral device. Subjects used a topical gel form of diclofenac 3%, 0.2% hyaluronic acid and 7.5% xylitol in an inert incipient. Subject 1 applied the diclofenac gel twice daily to the same location in the left buccal mucosa and wore a prototype device to hold the in place for 20 minutes, for a total of 7 days. Subject I performed a visual observation of the area of application daily and for 7 additional days following the application. Subject II applied the same topical gel form of diclofenac 3%, 0.2% hyaluronic acid and 7.5% xylitol in an inert incipient three times daily to an area of the right buccal mucosa and wore a prototype device for 20 minutes following each application, for 3 days.

Subject I reported experiencing a sensation of dryness in the buccal mucosa at the area of application for 1 hour after use for the first 3 days, and no other side effects. This dry sensation was no longer present after three days. Subject 2 reported a tingling of the lips for 30 seconds on expectorating the gel, but no other side effects. Visual inspection of the areas of topical application in both subjects showed no change from the topical medication.

Devices suitable for use in the present methods may have several individual components. They may be manufactured using a one mold or involve several separate parts. The first component of the device is an oral retention or fitting portion that functions to comfortably hold the device in the mouth by fitting over the teeth where it can be held for a predetermined period of time of treatment. The fitting portion of the device may fit over the upper teeth, the lower teeth, both the upper and lower teeth, or a portion of either or both the upper or lower teeth. This portion of the device may be pre-constructed to fit any size mouth. It is anticipated that several sizes of the device will be constructed to accommodate patients with larger or smaller mouth sizes, enhanced gag reflexes or oral pain. Alternatively, it may be made of a pliable material that can be fitted to the specific patient, either by the patient or by a medical professional such as a dentist. This portion of the device may be constructed of materials that will fit the needs of the device in terms of biocompatibility, ease of device cleaning, and the stability of the material within the mouth. The fitting portion may be made using materials, e.g., poly (methyl methacrylate), silicone rubber, polyurethane, and co-polymers of vinyl acetate or ethylene. Other materials include polyvinylacetate-polyethylene or ethylene vinyl acetate (EVA) copolymer, polyvinylchloride, latex rubber, acrylic resin and other laminated or non-laminated thermoplastics. In some embodiments, the materials for construction may also include a dual layering of a soft material on the inside portion and a hard acrylic outside portion that holds the device firmly to the teeth and forms a protective shell for the device.

One or more other covering portions of the device are designed to fit or cover at least the major parts of the mouth that are affected by the oral disease or disorder. These covering portions of the device may be constructed of soft materials that rest gently along the mucosa (lining) of the cheeks (called the buccal mucosa), the inner portions of the lips, the tongue (e.g., the ventral and sides), the palate and the mucosa underneath the tongue. These portions of the device may be constructed of materials such as silicone rubber, latex, synthetic polyisoprene, nitrile, polyurethane resin, plastic, polyester, acrylic resin pads, polypropylene, low density polyethylene, and various laminates or layered soft/soft laminates. In some embodiments, laminates may feature a top layer of denser vinyl for memory and abrasion resistance and a soft pliable bottom layer for patient comfort.

The covering portion of the device may include an additional layer of semi-porous material that will be in contact with the oral mucosa. This will allow for anti-leukoplakia agents (e.g., the oral gel composition described herein) to be placed or disposed on the device, so they may be gradually released onto the affected tissue. Representative examples of materials that may be used for this part of the device include materials used for wound dressings such as thin, semi-permeable polyurethane films coated with a layer of acrylic adhesive. Other materials, such as gels may be incorporated into the mucosal (i.e., inner) side of the covering portion of the device. The use of gels allows a soft, generally water-soluble material to adhere to this portion of the device. Active agents such as antibiotics and local pain relieving drugs can be mixed into or incorporated into the matrix of the gels. Examples of such gels include carboxymethylcellulose-based gels and alginate-based gels. In some embodiments, the inner portion may include foam-like materials. Foam materials provide a soft interface with the affected oral mucosa. Active agents may be held within the matrix of these foam-like materials. In addition, the material used for the internal layer of the covering portion of the device that is in contact with the mucosa may include drug-eluting fibers. These may include monolithic polymer fibers and reservoir fibers such as polyactic acid (PLLA) in which the drug is dissolved or dispersed. Other materials that may be used for the internal portion of this part of the device include nanoporous materials such as ceramics, composites, metals, and polymeric organic substances. Other examples of materials include nanoporous oxides, including alumina, titania, silica, zirconia, polycarbonate, polyethylene terephthalate, polysulfide and polymers combined with ceramics. Nanoporous materials may be produced by anodization, lithography, focused ion beam etching, ion-tracking etching, phase separation and sol-gel processes. Alternatively, the covering portions of the device may contain ridges, indentations or an abrade surface that will allow topical medication to remain for a longer period of time within the device when in contact with the affected mucosa.

Thus, in some embodiments, the device may have an upper part that fits on upper teeth (e.g., upper front teeth) and has a covering portion that drapes across the palate and the inner part of the upper lip. The device may have a lower part that fits on lower teeth (i.e., lower front teeth) and has a covering portion that drapes across the sublingual mucosa, the sides and/or underportion of the tongue, and inner portions of the cheek (the buccal mucosa). Devices may also have adjustable components that allow the device to fit snugly and comfortably in the mouth of an affected patient. Thus, both the upper and lower parts of the device may contain a system that allows for adjustment of these portions of the device to fit comfortably in the mouth. Adjustments can be made to shorten or lengthen the device as well as to elevate of lower the device to assist with fitting of the apparatus for comfortable and prolonged use.

Additional modifications of the device may be made in order to optimize fitting in the mouth and for individualizing the construction of the device based on the patient's oral anatomy. Such modifications may be made with the use of imaging methods such as radiographic procedures and 3-dimensional photographic imaging. Furthermore, the use of dental-type molds may be used to optimize sizing of the device for individual patients. Yet further modifications may include addition of materials such as padding and anchoring portions of the device to add to the comfort level of its use. Other modifications may be made based on methods to size the individual portions of the device to optimize covering of the affected area of the oral mucosa. Further modifications may be performed to allow the device to be worn overnight. The device will be constructed in multiple sizes, with appropriate adjustment of the dimensions of its individual components to accommodate patients with smaller and larger mouths, heightened gag reflexes and sensitivity to devices that are placed in the mouth.

Furthermore, because oral leukoplakia affects specific, discreet areas of the mouth in individual patients, the device is designed such that covering portions of the device that are designed for the coverage of areas of the mucosa that are not affected in an individual patient can be removed by the cutting these portions away. This will increase the confort of wearing the device.

The active agents may be applied to the covering portion(s) of the device that come into contact with the affected mucosal tissue. The use of indented or pitted surfaces, irregular or roughened surfaces to increase surface area of these portions of the device, semi-porous materials to line these portions of the device, imparts sustained release properties to the device which allow for gradual and prolonged exposure of the mucosa to the agents. In some embodiments, the medications may be first applied to the affected area(s), followed by placement of the device in the mouth. Using this method, the device holds the medications in place and allows their prolonged contact with the mucosa.

An oral treatment device 200, as shown in FIG. 1, in accordance with an aspect of the present disclosure, is suitable for use with the methods described herein. The device 200 may have several individual components or portions, however, it should be noted that "component" does not necessarily mean a separate piece or pieces unless specifically set forth as such. The device 200 includes a curved, or arcuate, oral retention or fitting portion or body 204 that can be comfortably held for a predetermined period of time or treatment. The fitting portion 204 of the device 200 has an arc that generally corresponds to the arrangement of teeth in the human mouth, i.e., the dental arche, and may fit over the upper teeth, the lower teeth, both the upper and lower teeth or a portion of either or both the upper or lower teeth.

The device 200 may be preconstructed to fit any size mouth. Alternatively, it may be made of a pliable material that can be fitted to the specific patient, either by the patient or by a medical professional such as a dentist. The device 200 may be constructed of materials that meet biocompatibility requirements for human use, ease of device cleaning and the stability of the material within the mouth. The device 200 may be made using materials including, silicone rubber, poly (methyl methacrylate), polyurethane and co-polymers of vinyl acetate or ethylene. Other materials that could be used include polyvinylacetate-polyethylene or ethylene vinyl acetate (EVA) copolymer, polyvinylchloride, latex rubber, acrylic resin and other laminated or non-laminated thermoplastics.

The device 200 includes symmetrically provided covering portions 208, each having an upper wing portion 212 and a lower wing portion 216 configured to fit or cover parts of the mouth that are affected by leukoplakia. These covering portions 208 of the device 200 are generally more flexible (e.g., compliant or softer) than the body portion 204 by, for example, being thinner than the body portion 204 or being of a different material. The covering portions 208 may rest along the sensitive mucosa (lining) of the cheeks (called the buccal mucosa), the inner portions of the lips, the palate and the mucosa to the sides of and underneath the tongue. These areas may contain ridges or surface indentations to prolong adherence of topical medications.

These covering portions 208 of the device 200, in one aspect of the present disclosure, may be constructed of materials, in addition to those materials listed above, such as silicone rubber, latex, synthetic polyisoprene, nitrile, polyurethane resin, silicone rubber, plastic, polyester, acrylic resin pads, silicone, polypropylene, low density polyethylene and various laminates or layered soft/soft laminates. In some embodiments, laminates may feature a top layer of denser vinyl for memory and abrasion resistance and a soft pliable bottom layer for patient comfort. Further, the choice of materials for the device 200 provides a predetermined amount of "spring load" that urges the covering portions 208 outward as represented by the arrows A in FIG. 3.

The covering portions 208 of the device 200 have an exterior surface 220 that may include an additional layer 224 of semi-porous material that will be in contact with the oral mucosa. This semi-porous layer 224 will allow for anti-leukoplakia agents to be placed or disposed on the device 200, in order to be gradually released onto the affected tissue. Representative examples of materials that may be used for this part of the device include materials used for wound dressings such as thin, semi-permeable polyurethane films coated with a layer of acrylic adhesive.

Other materials, such as gels, may be incorporated onto the exterior surface 220 of the covering portion 208 of the device 200. The use of gels allows a soft, generally water-soluble material to adhere to this portion of the device 200. Medications such as antibiotics and local pain relieving drugs can be mixed into or incorporated into the matrix of the gels. Examples of such gels include carboxymethylcellulose-based gels and alginate-based gels.

Referring again to FIG. 1, each covering portion 208 and its respective upper and lower wing portions 212, 216 are made of softer or more flexible material, as set forth above. The upper wing portions 212 extend above the upper gum line to cover or contact a portion of the upper inner cheek, and the inner upper lip, while the lower wing portions 216 extend below the lower gum line to cover or contact a portion of the lower inner cheek. In addition, the upper and lower wing portions 212, 216 cover the openings for the parotid duct and a number of salivary glands.

In one embodiment of the device 200, a portion of the external surface 220 may be treated to provide a micro-textured surface 240 that results in small reservoirs being created, as shown in FIG. 1. The micro-textured surface 240 may be provided in the device 200 by etching a pattern into the mold that is used to make the device 200. Alternatively, the external surface 220 of the device 200 may be modified by etching or sand-blasting once freed from the mold. These small reservoirs serve to retain in place therapeutic materials (e.g., the oral gel composition described herein) that have been applied to the inner cheek to treat leukoplakia. Advantageously, the medicine is then in place longer before it is washed away by saliva. Alternatively, the therapeutic material may be "loaded" onto the micro-textured surface 220 before the device 200 is placed in the mouth which may aid in application to the inner mucosa.

In some embodiments, the covering portion 208 may include foam-like materials. Foam materials provide a soft interface with the affected oral mucosa. Medications (e.g., the oral gel composition described herein) may be held within the matrix of these foam-like materials.

In addition, the material used for the exterior surface 220 of the covering portions 208 of the device 200 that is in contact with the mucosa may include drug-eluting fibers. These fibers may include monolithic polymer fibers and reservoir fibers such as polylactic acid in which the drug is dissolved or dispersed.

Still further, other materials that may be used on the exterior surface 220 of the covering portion 208 include nanoporous materials such as ceramics, composites, metals and polymeric organic substances. Other examples of materials include nanoporous oxides, including alumina, titania, silica, zirconia, polycarbonate, polyethylene terephthalate, polysulfide and polymers combined with ceramics. Nanoporous materials may be produced by anodization, lithography, focused ion beam etching, ion-tracking etching, phase separation and sol-gel processes.

The body portion 204 includes an upper portion configured to cover the mucosa between the upper teeth and the gums and the inside of the upper inner lip. Advantageously, this aids in retention of the device 200 within the mouth by holding it in place between the upper inner lips and upper teeth. Alternatively, the device may be worn to over the lower teeth and gums and the inside of the lower lip. This portion is constructed of thinner or more pliable material for comfort and for holding medication in place in that area of the mouth.

Figure 2:
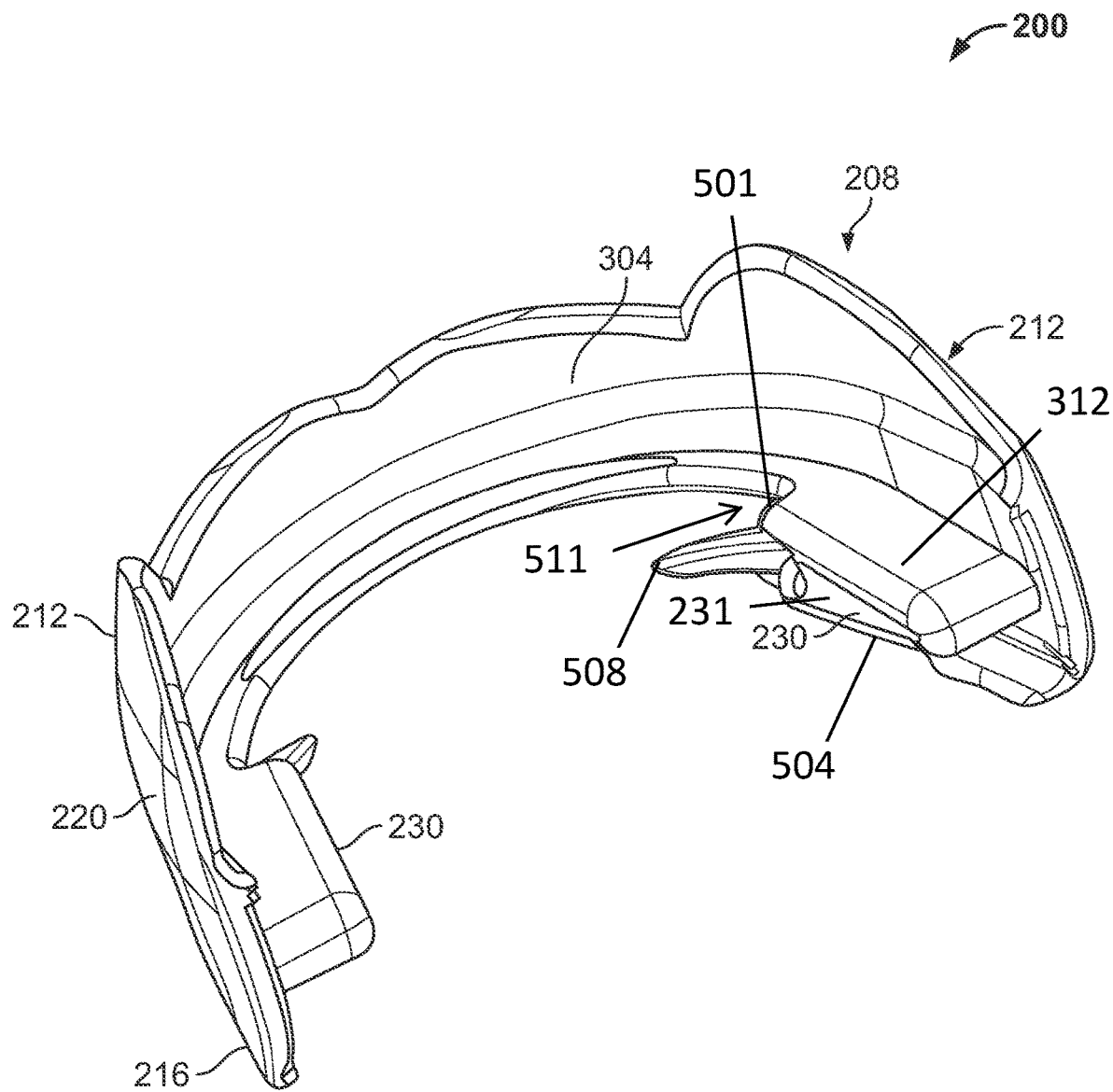
FIG. 2 is a rear perspective view of the device of FIG. 1.
Figure 4:
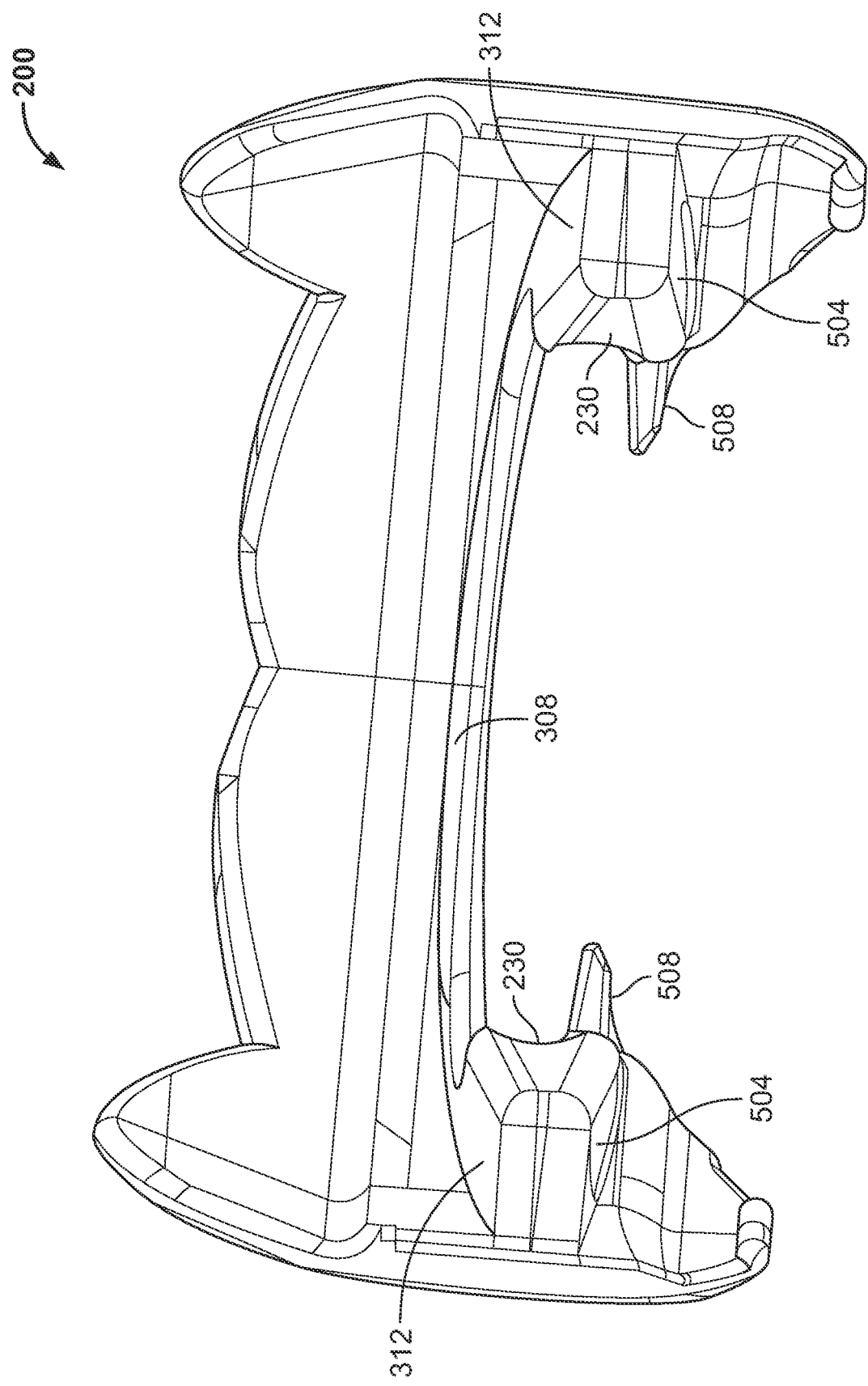
FIG. 4 is a rear perspective view of the device of FIG. 1.

Referring to FIGS. 2 and 4, each of which is a rear perspective view, the device 200 may include symmetrically opposed bite flanges 230 that extend from an interior surface 304. In addition, an upper ledge 308 also extends from the interior surface 304 and when the device 200 is placed in the mouth of a patient, the upper teeth of the patient may rest thereon.

Figure 3:
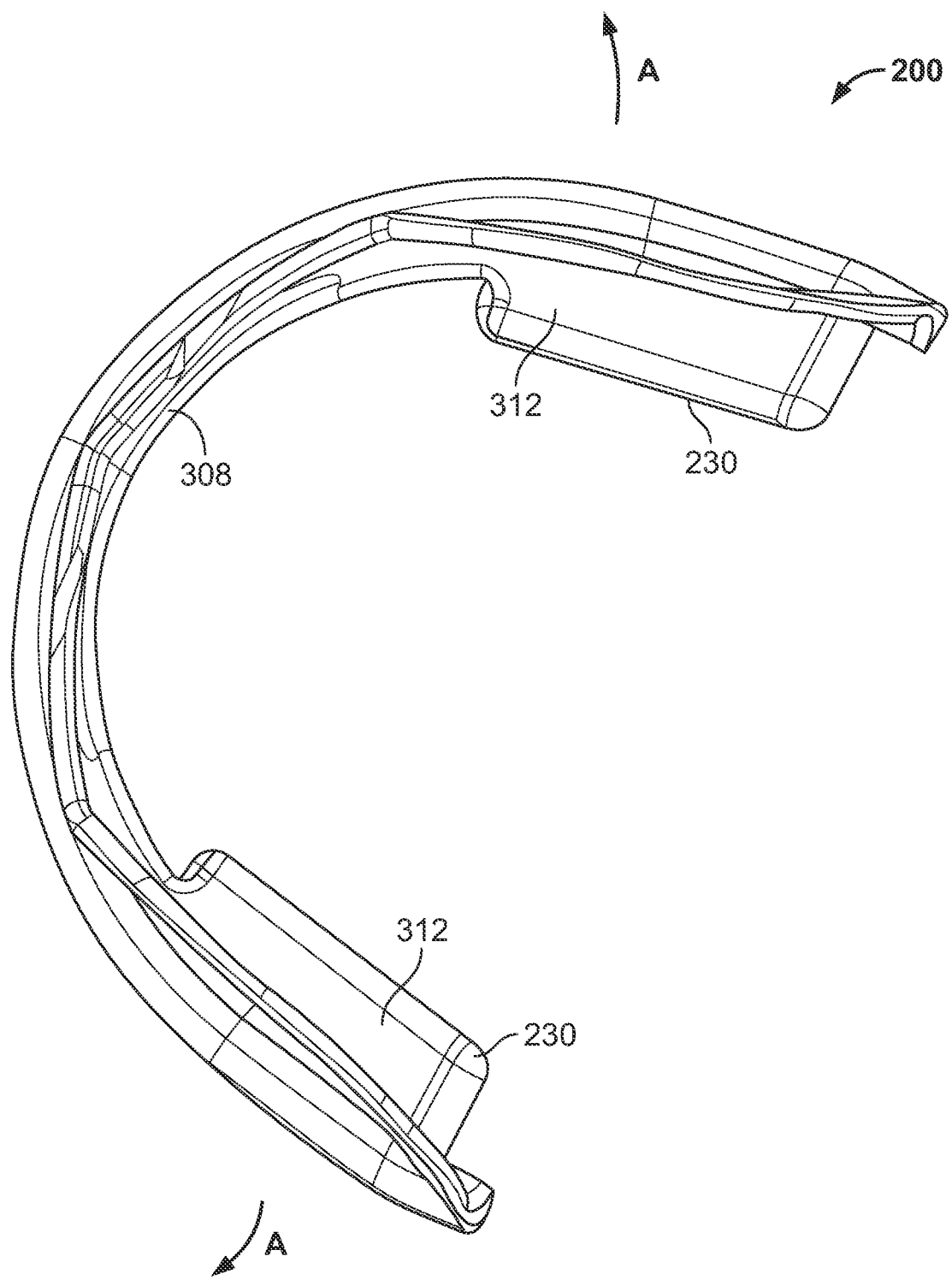
FIG. 3 is a top view of the device of FIG. 1.

As shown in FIGS. 1-3, which is a top view of the device 200, the upper ledge 308 is continuous around an inner arc of the device 200 and is contiguous with an upper bite surface 312 of the bite flanges 230. Each bite flange 230 includes a lower bite surface 504 that, in conjunction with the upper bite surface 312, forms a bite wedge shape 231. When the device 200 is placed in the patient's mouth, the top teeth will rest on the upper ledge 308 and some of the upper and lower back teeth, e.g., mid-molars, can bite down on the upper and lower bite surfaces 312, 504 of the bite flange 230. In this manner, the device 200 can be held in place with minimal effort. The bite flange 230 is desired for comfort to allow the patient to bite down on the device without becoming fatigued too quickly during the time that the medication is held in place. In addition, each lower wing portion 216 further includes a v-shaped notch 501 being positioned adjacent each bite wedge 231 towards the middle section 204. Wherein, the lower surface edge along the middle section of the fitting portion extends arcuately towards each lower wing portion the v-shaped notch 501 defines a gap 511 between the lower surface edge and the lower tab 508 extending from the lower bite flange 504.

Figure 5:
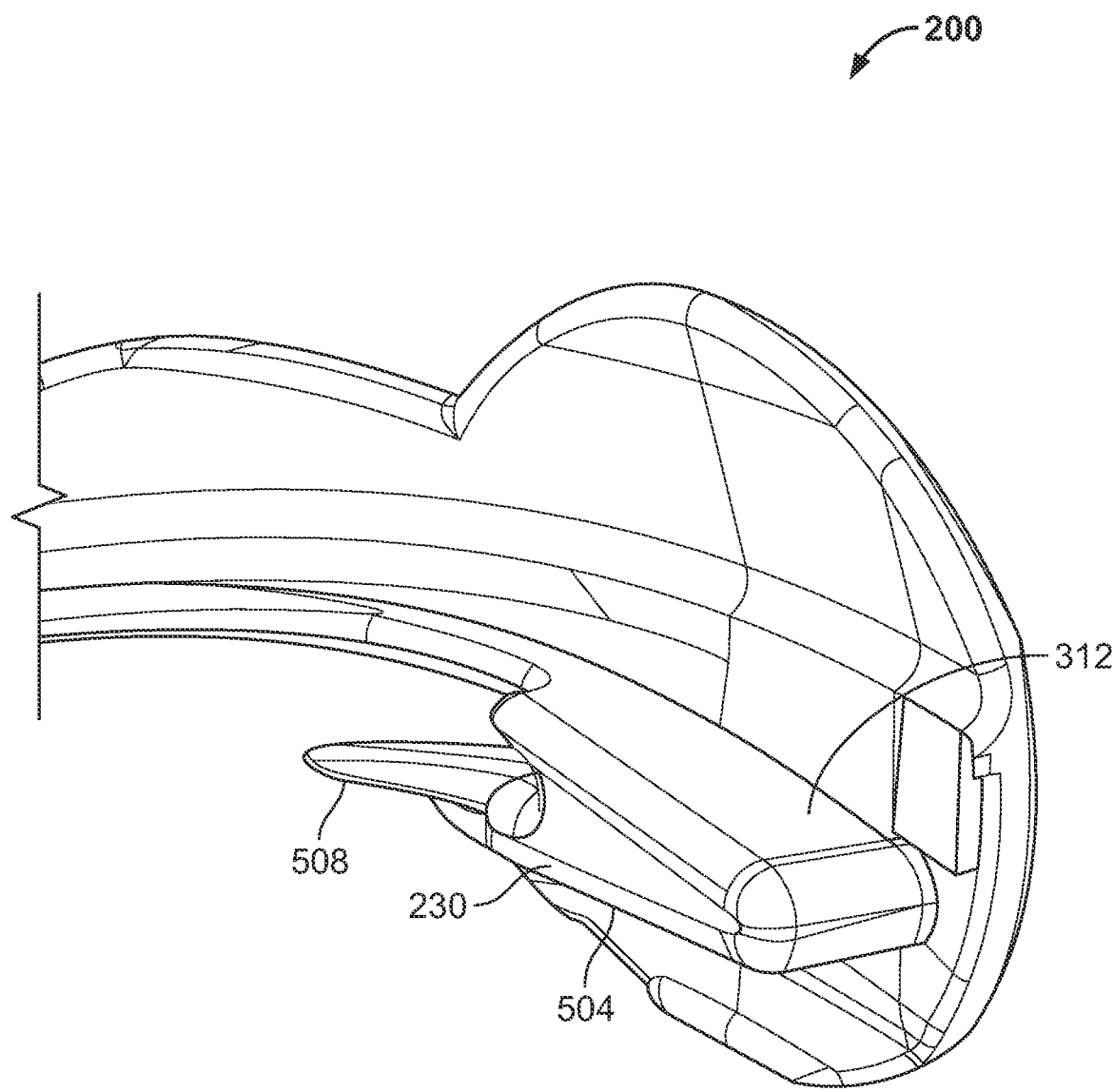
FIG. 5 is a magnified rear perspective view of a portion of the device of FIG. 1.

As shown in FIGS. 4 and 5, and as seen from the back of the device 200, symmetric lower tabs 508 are provided forward of each respective bite flange 230. The lower tabs 508 rest on some of the lower teeth forward of those that are biting down on the bite flanges 230. The lower tabs 508 provide additional stability and absorb some stress from the patient holding on, i.e., biting down, on the bite flanges 230.

Figure 6:
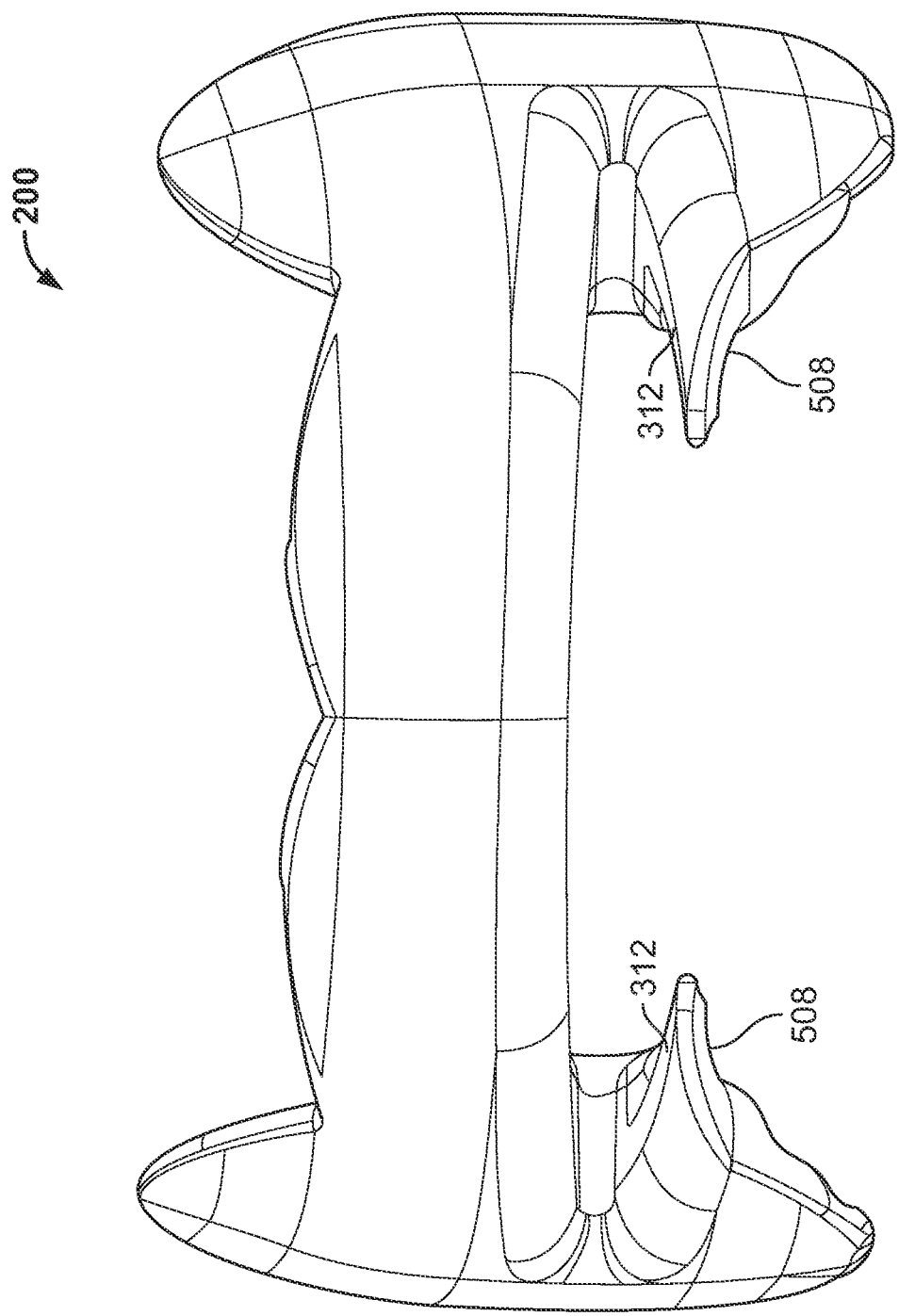
FIG. 6 is a front view of the device of FIG. 1.

As shown in FIG. 6, which is a front view of the device 200, the lower tabs 508 may extend around a portion of the arc of the lower teeth. In another embodiment, the lower tabs 508 may extend all the way around the arc into a single lower tab, i.e., a continuous piece for all of the lower teeth to contact.

Figure 7:
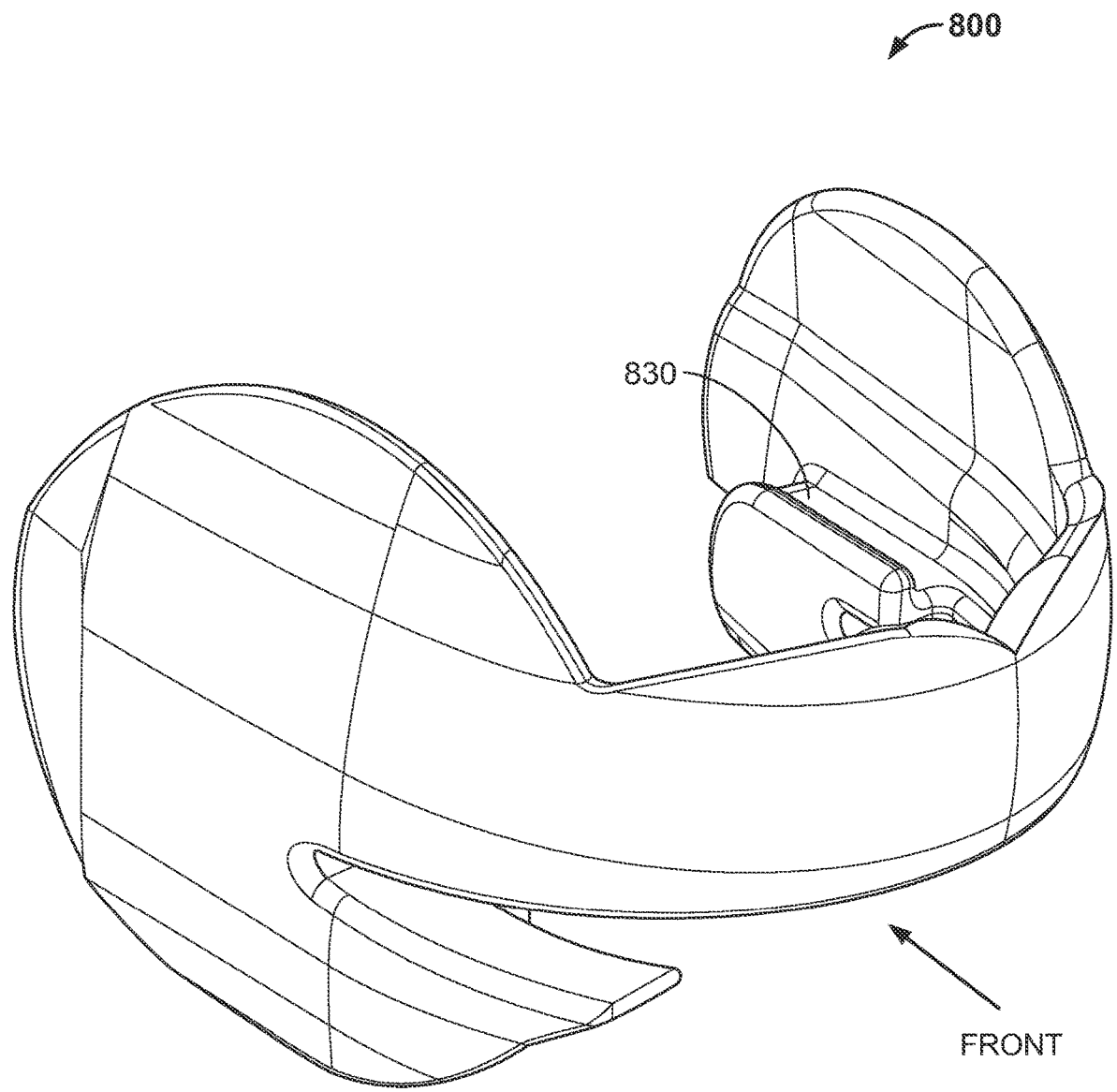
FIG. 7 is a front perspective view of a leukoplakia treatment device, in accordance with another aspect of the present disclosure.

Referring now to FIG. 7, another leukoplakia treatment device 800, in accordance with an aspect of the present disclosure that is suitable for use with the methods described herein is presented from a front perspective view. The device 800 is similar to the device 200 as set forth above, however, the device 800 includes symmetrically opposed bite flanges 830 that differ from the bite flanges 230 described above.

Figure 8:
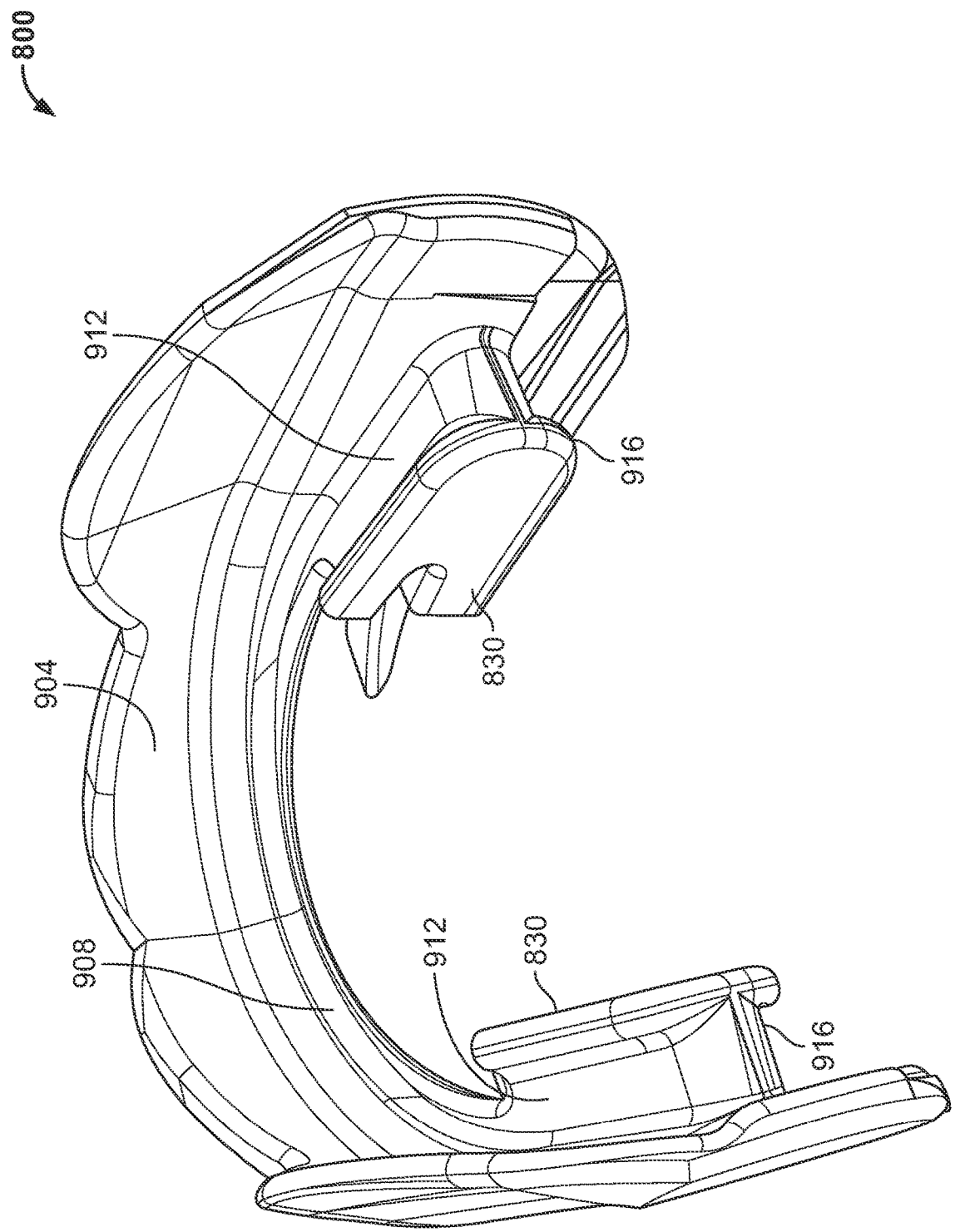
FIG. 8 is a rear perspective view of the device of FIG. 7.
Figure 9:
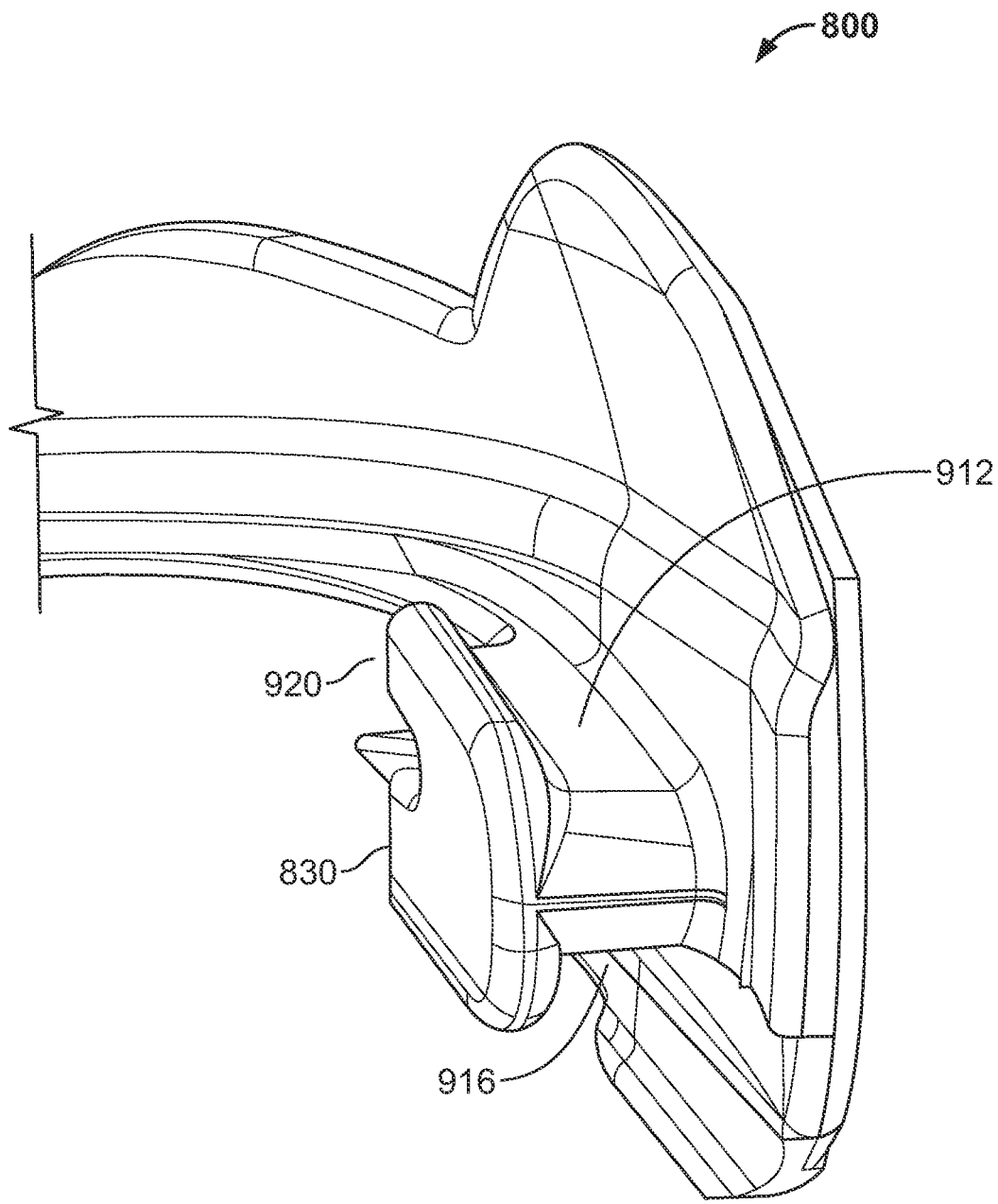
FIG. 9 is a magnified rear perspective view of a portion of the device of FIG. 7.

As shown in FIGS. 8 and 9, the bite flanges 830 extend from an interior surface 904. An upper ledge 908 also extends from the interior surface 904 and when the device 800 is placed in the mouth of a patient, the upper teeth of the patient may rest thereon. The upper ledge 908 is continuous around an inner arc of the device 800 and is contiguous with an upper bite surface 912 of the bite flanges 830. Each bite flange 830 includes a lower bite surface 916. When the device 800 is placed in the patient's mouth, the top teeth will rest on the upper ledge 908 and some of the upper and lower back teeth, e.g., mid-molars, can bite down on the upper and lower bite surfaces 912, 916 of the bite flange 830. In this manner, the device 800 can be held in place with minimal effort. Each bite flange 830 is made of softer or spongier material that the patient can bite down on without becoming fatigued too quickly.

In addition to the upper and lower bite surfaces 912, 916, the bite flange 830 includes a guide ridge 920 that is generally transvers to the upper and lower bite surfaces 912, 916. The guide ridge 920 provides a space to line up the upper teeth in order to maintain the device 800 in position. Advantageously, the patient need not bite down on the bite flange 830 to keep the device 800 in place in the mouth with the side portions positioned against the inner cheeks.

Figure 10:
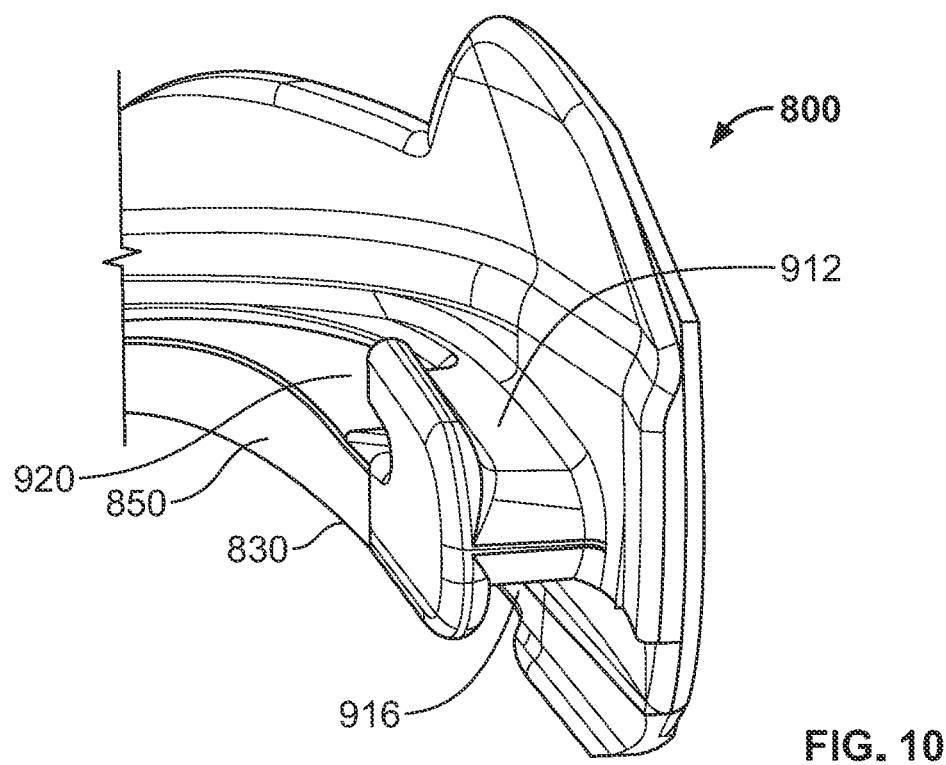
FIG. 10 is an inside view of the right portion of the device of FIG. 10 which includes a covering portion for the front and lateral portions of the tongue.

FIGS. 10-15 illustrate a device that is a modified version of FIG. 7 and which includes a covering portion for the front and lateral portions of the tongue. FIG. 10 is an inside view of the right portion of the device. This form of the device includes a soft covering portion (850) for the lateral and front of the tongue that follows the arcuate design of the device. This soft covering portion for the lateral tongue is attached to the inferior portion of the bite flange (830), is a thicker depth than the covering wings. Part 850 rests comfortably and wraps around the lateral portions of the tongue, forming a covering over the sides and front of the tongue.

Figure 11:
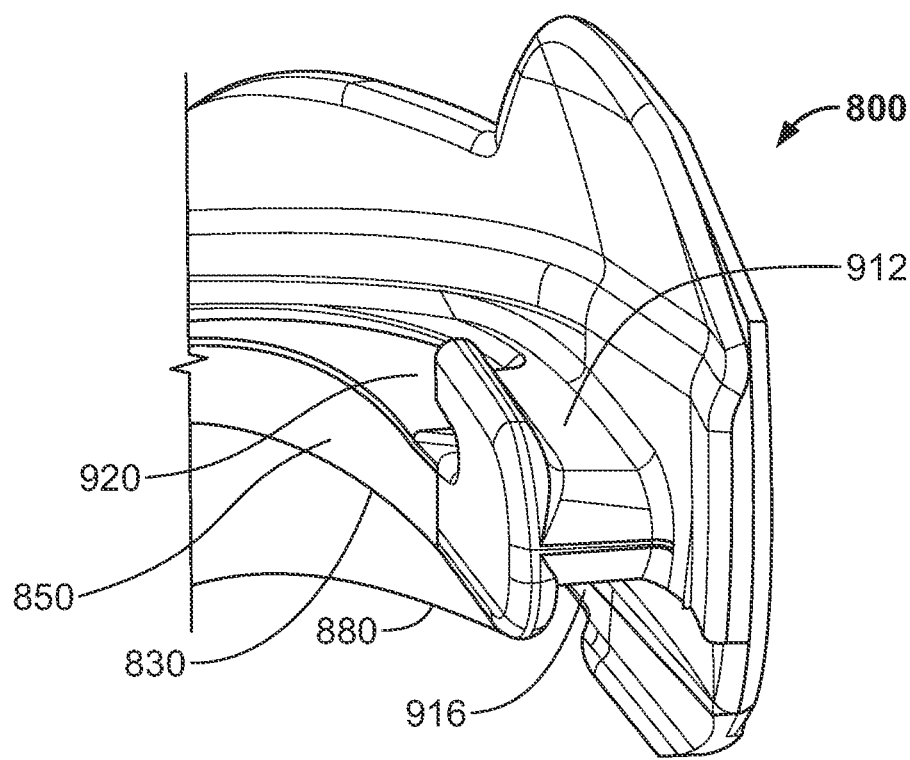
FIG. 11 is an inside view of the right portion of the device of FIG. 10 which also shows the portion that covers the area beneath the tongue and floor of the mouth inside of the teeth.

FIG. 11 is an inside view of the right portion of the modified device. This form of the device includes a soft covering portion (850) for the lateral and front of the tongue that is attached to the inferior part of the bite flanges (830) and follows the arcuate design of the device. It also shows the portion (880) that covers the area beneath the tongue and floor of the mouth inside of the teeth. This is a wing-like portion of the device with similar thin structure and fits under the tongue. It is attached to both the inferior portion of the bite flanges (830) and to the inferior portion of the lateral tongue covering portion (850) of the device. The tongue can be slipped into combined portions (850) and (880), thus providing coverage of the lateral tongue, the ventral tongue and the mucosa of the floor of the mouth inside of the teeth.

Figure 12:
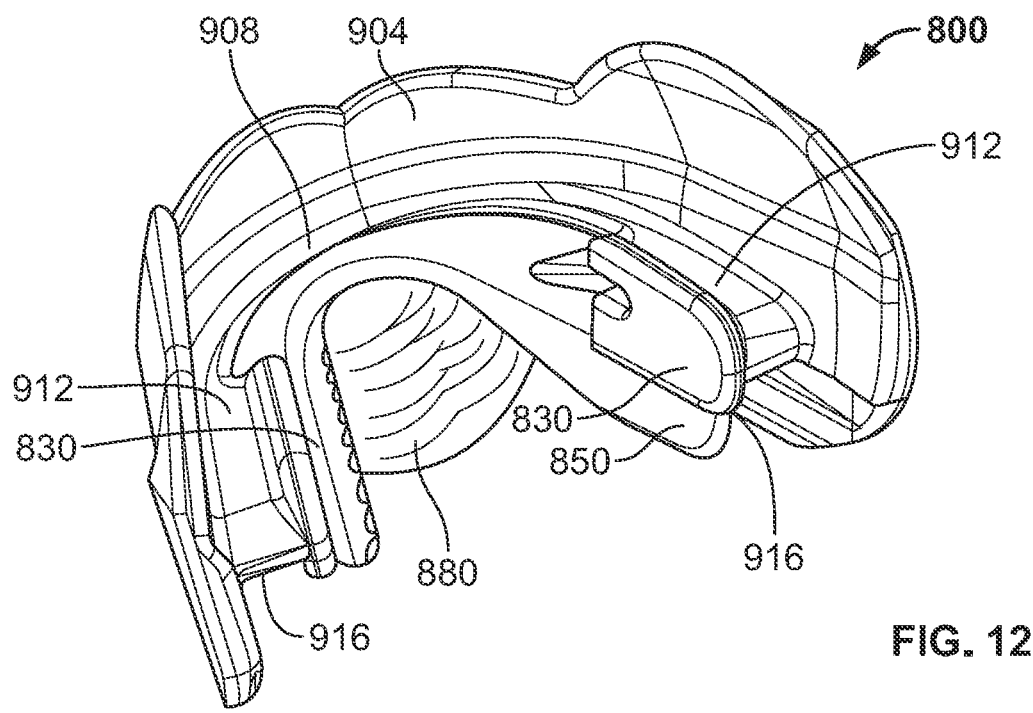
FIG. 12 is a posterior superior view of the device of FIG. 11.

FIG. 12 is a posterior superior view of the device of FIG. 11. This view demonstrates the soft covering portion (850) for the later and front of the tongue that is attached to the inferior part of the bite flanges (830) and follows the arcuate design of the device. It also shows the portion (880) that covers the area beneath the tongue and floor of the mouth inside of the teeth. This is a wing-like portion of the device and has a similar thin structure to the cheek and inner lip covering wings and fits under the tongue. It is attached to both the inferior portion of the bite flanges (830) and to the inferior portion of the lateral tongue covering portion (850) of the device.

Figure 13:
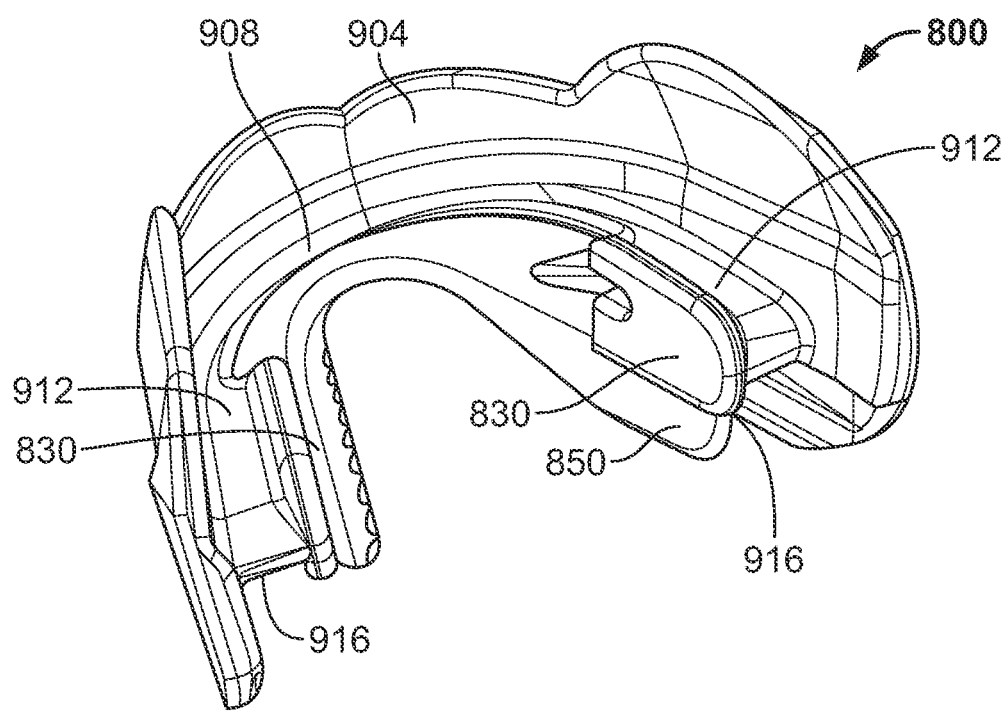
FIG. 13 is a posterior superior view of the device of FIG. 10.

FIG. 13 is a posterior superior view of the device of FIG. 10. This view shows the soft covering portion (850) for the lateral and front of the tongue that is attached to the inferior part of the bite flanges (830) and follows the arcuate design of the device.

Figure 14:
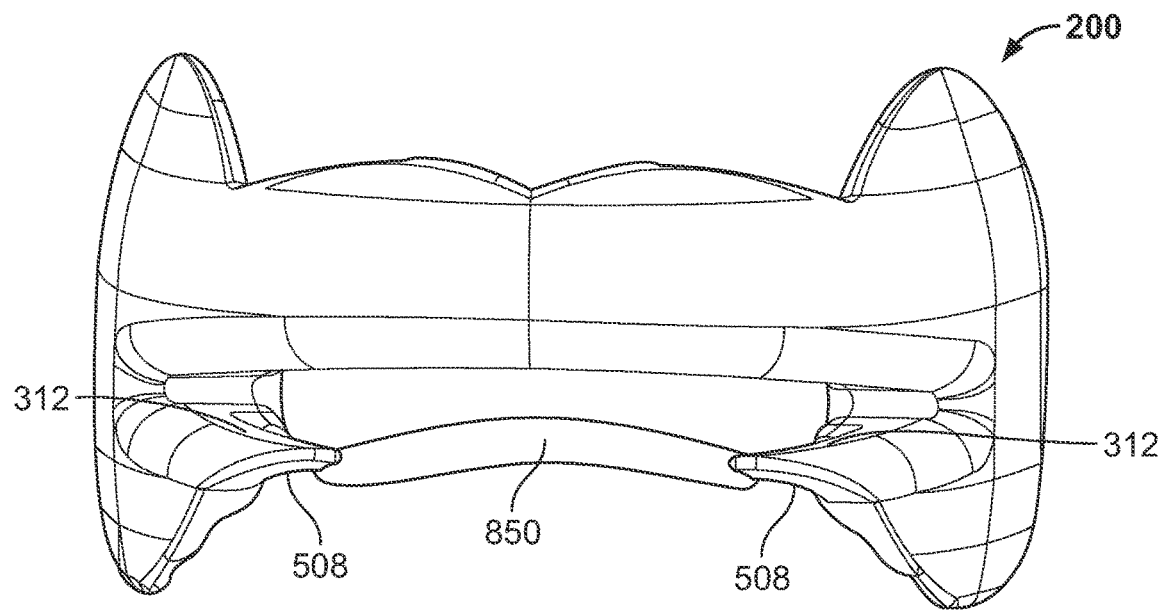
FIG. 14 is a posterior view of the device of FIG. 10.

FIG. 14 is a posterior view of the device of FIG. 10. This view demonstrates the soft covering portion (850) for the lateral and front of the tongue that is attached to the inferior part of the bite flanges (830) and follows the arcuate design of the device. This design allows portion (850) to easily rest on the sides and front of the tongue.

Figure 15:
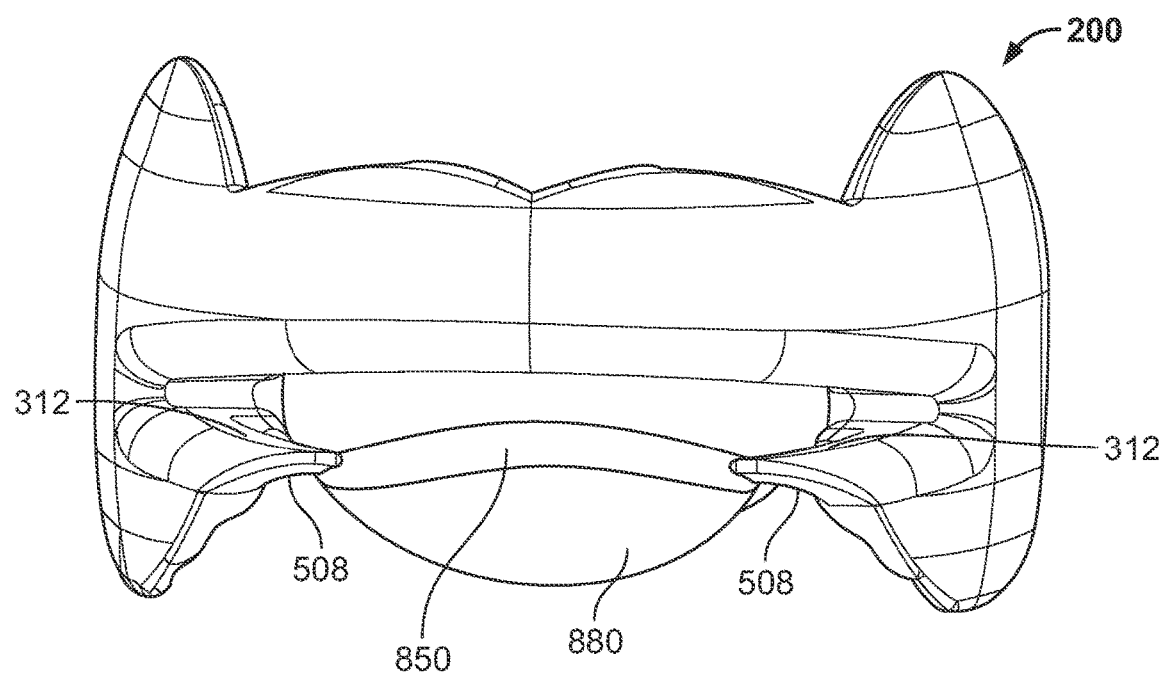
FIG. 15 is a posterior view of the device of FIG. 11.

FIG. 15 is also a posterior view of the device of FIG. 11. This view demonstrates the soft covering portion (850) for the later and front of the tongue that is attached to the inferior part of the bite flanges (830) and follows the arcuate design of the device. It also shows the portion (880) that covers the area beneath the tongue and floor of the mouth inside of the teeth. This is a wing-like portion of the device has a similar thin structure to the cheek and inner lip wings and fits under the tongue. It is attached to both the inferior portion of the bite flanges and to the inferior portion of the lateral tongue covering portion (850) of the device.

Additional modifications of the device may be made in order to optimize fitting in the mouth and for individualizing the construction of the device based on the patient's oral anatomy. Individualization can be accomplished by the construction of devices in several sizes to accommodate patients with different size mouths and abilities to tolerate the presence of an oral device inside of the mouth. Further modifications may be made with the use of imaging methods such as radiographic procedures and 3-dimensional photographic imaging. Furthermore, the use of dental-type molds may be used to optimize sizing of the device for individual patients. Yet further modifications may include addition of materials such as padding and anchoring portions of the device to add to the comfort level of its use. Other modifications may be made based on methods to size the individual portions of the device to optimize covering of the affected area of the oral mucosa.

Advantageously, the designs of the devices described above follow the contour of the mouth for comfort. The bite flanges provide surfaces for both the upper and lower teeth to close on and hold the device in place. In one aspect, the device is configured to be located over only the upper teeth as this provides additional comfort compared to devices that fit over both the upper and lower teeth, in addition to making it easier for the patient to breathe while the device is in place. Still further, a device where only the upper teeth are covered allows for easy elimination of saliva without the necessity to remove the device. Alternatively, the device may be worn to fit only the lower teeth with similar benefits.

The side portions between teeth, gums and inner lips provide coverage of gums, upper oral mucosa and inside of upper lip and a portion of the lower lip allowing for increased mucosal coverage and which also helps to hold the device in place. Alternatively, the device may worn so that the side portions cover the gums, lower oral mucosa and inside of the lower lip. Bolstering of the mouth is an additional feature that promotes retention of topical medications used for the treatment of oral leukoplakia.

The active (e.g., the oral gel composition described herein) agents may be applied to the covering portion(s) of the device that come into contact with the affected mucosal tissue. The use of semi-porous materials to line these portions of the device, imparts sustained release properties to the device that allow for gradual and prolonged exposure of the mucosa to the agents. In some embodiments, the medications (e.g., the oral gel composition described herein) may be first applied to the affected area(s), followed by placement of the device in the mouth. Using this method, the device holds the medications in place and allows their prolonged contact with the mucosa.

When the device is held within the mouth, the oral gel composition described herein remains in contact with the oral mucosa that is affected by leukoplakia for a predetermined time or treatment period which for purposes of the present invention, may include a contact time of 10 minutes, 20 minutes, 30 minutes, 60 minutes, 90 minutes, or more. In some embodiments, methods entail the device being held in the mouth for about 10 minutes to up to 2 hours at a time. The method may be conducted multiple times per day, for example, but not limited to, from 1-4 times daily.

With respect to embodiments of the present invention that are directed to treatment of oral leukoplakia, the oral gel composition described herein is topically administered to mucosal tissue in a therapeutically effective amount. As persons skilled in the art would appreciate, this amount will vary depending upon the agent itself and other factors which may include one or more of the severity factors of the condition and the general health of the patient. The therapeutic amount may be effective to ameliorate one or more symptoms presented by the patient, e.g., mucosal redness, abnormal white mucosa, and oral ulcerations, or even cure the condition.

With respect to aspects of the present invention that are directed to prophylactic uses, the oral gel composition described herein is topically applied to mucosal tissue of a patient suitably prior to an event that is known to induce oral leukoplakia, e.g., poor dental hygiene, in a prophylactically effective amount. This amount may be effective to delay or inhibit the onset of leukoplakia or reduce the severity or duration of leukoplakia or any symptom associated therewith, or even preventing the onset of the condition. Representative examples of patients or subjects who are prone to or at risk of developing oral leukoplakia include persons who may have a prior history of cancer of the head and neck or esophagus or may be heavy users of tobacco products (chew, cigarettes and cigars), users of large amounts of alcohol, chewers of betel nuts, or those with a history of oral HPV infection. Here again, in these aspects of the present invention, persons skilled in the art will appreciate that prophylactically effective amounts will vary depending upon factors which may include one or more of the severity of the condition and the general health of the patient.

Another aspect of the present disclosure provides a kit for administering the oral gel composition described herein to the mucosal tissue of an individual. The kit may include a device, as described above, one or more dosage amounts of the oral gel composition which may be disposed in a container such as a squeezable tube, an applicator (e.g., oral swab, Toothette®, and blu®m oral gel applicator) to more accurately apply the medication onto the mucosa that is affected by oral leukoplakia and instructions regarding the method of using the device and the agent to treat the affected mucosal tissue area.

Although aspects of the present invention herein have been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed:

1. A method of treating a patient with oral leukoplakia or at risk of developing oral leukoplakia, the method comprising:

administering a therapeutically effective amount of an oral gel composition comprising a nonsteroidal anti-inflammatory drug (NSAID) or a pharmaceutically acceptable salt thereof, hyaluronic acid or a pharmaceutically acceptable salt thereof, a gelling agent or thickener, and a flavoring agent and/or sweetener to a mucosal tissue or an affected portion thereof; and inserting, in a mouth of the patient, a device comprising:
an oral retention portion that is suitably shaped to be retained in an oral cavity for a predetermined treatment period, an upper bite flange and a lower bite flange extending from an interior surface of the oral retention portion forming a bite wedge along each end defined by oral retention portion, and a covering portion that extends from the retention portion, the covering portion has at least one surface that contacts the mucosal tissue being treated with the oral gel composition therapeutic agent.

2. The method of claim 1, wherein administering the therapeutically effective amount of the oral gel composition comprises:
administering the therapeutically effective amount of the oral gel composition to a patient with oral leukoplakia.

3. The method of claim 2, wherein administering the therapeutically effective amount of the oral gel composition comprises administering the therapeutically effective amount of the oral gel composition to a patient at risk of developing oral leukoplakia.

4. The method of claim 3, wherein administering the therapeutically effective amount of the oral gel composition comprises:
applying the oral gel composition to the mucosal tissue or a portion of the mucosal tissue prior to inserting the device in the mouth of the patient;
applying the oral gel composition to an outer surface of the device prior to inserting the device in the mouth of the patient and then inserting the device in the mouth of the patient; or prior to inserting the device in the mouth of the patient:
applying a first amount of the oral gel composition to the mucosal tissue or the portion of the mucosal tissue; and
applying a second amount of the oral gel composition to the outer surface of the device and then inserting the device in the mouth of the patient.

5. The method of claim 4, wherein the oral device comprises:
a fitting portion having an arcuate shape corresponding to a dental arche of the patient and at least one covering portion, the covering portion having a respective outer surface, an upper wing portion and a lower wing portion;
at least one bite flange extending from an interior surface of the fitting portion;
an upper ledge extending from the interior surface of the fitting portion and following the arc of the fitting portion,
wherein an upper surface of the upper ledge and an upper surface of the at least one bite flange are continuous with one another,
wherein the at least one covering section is more flexible than the fitting portion, and wherein a portion of the respective outer surface of the at least one covering portion is in contact with the portion of the mucosal tissue.

6. The method of claim 5, wherein the at least one covering portion has a surface that contacts and rests against an affected portion of a tongue of the patient.

7. The method of claim 6, wherein the at least one covering portion has a surface that contacts and rests against a ventral side of the tongue.

8. The method of claim 6, wherein the at least one covering portion has a surface that contacts and rests against one or both sides of the tongue.

9. The method of claim 6, further comprising cutting away covering portions that are designed to cover portions of the mucosa that do not have oral leukoplakia, for patient comfort.

* * * * *